(12) United States Patent
Li

(10) Patent No.: US 7,990,534 B2
(45) Date of Patent: Aug. 2, 2011

(54) SYSTEM AND METHOD FOR AZIMUTH ANGLE CALIBRATION

(75) Inventor: Shifang Li, Pleasanton, CA (US)

(73) Assignee: Tokyo Electron Limited, Tokyo (JP)

( * ) Notice: Subject to any disclaimer, the term of this patent is extended or adjusted under 35 U.S.C. 154(b) by 637 days.

(21) Appl. No.: 12/169,331

(22) Filed: Jul. 8, 2008

(65) Prior Publication Data

US 2010/0010765 A1  Jan. 14, 2010

(51) Int. Cl.
*G01J 4/00* (2006.01)
(52) U.S. Cl. ......................................................... 356/364
(58) Field of Classification Search .................. 356/364; 250/559.09
See application file for complete search history.

(56) References Cited

U.S. PATENT DOCUMENTS

| | | | |
|---|---|---|---|
| 6,433,878 B1 | 8/2002 | Niu et al. | |
| 6,538,731 B2 | 3/2003 | Niu et al. | |
| 6,778,273 B2 | 8/2004 | Norton et al. | |
| 6,785,638 B2 | 8/2004 | Niu et al. | |
| 6,891,626 B2 | 5/2005 | Niu et al. | |
| 6,943,900 B2 | 9/2005 | Niu et al. | |
| 7,064,829 B2 | 6/2006 | Li et al. | |
| 7,224,471 B2 * | 5/2007 | Bischoff et al. | ............... 356/601 |
| 7,280,229 B2 | 10/2007 | Li et al. | |
| 7,414,733 B2 * | 8/2008 | Bischoff et al. | ............... 356/601 |
| 2004/0267397 A1 | 12/2004 | Doddi et al. | |
| 2005/0192914 A1 | 9/2005 | Drege et al. | |
| 2005/0209816 A1 | 9/2005 | Vuong et al. | |

OTHER PUBLICATIONS

U.S. Appl. No. 12/050,053, filed Mar. 17, 2008 for Tian et al.
U.S. Appl. No. 12/050,919, filed Mar. 18, 2008 for Tian et al.
U.S. Appl. No. 12/057,316, filed Mar. 27, 2008 for Tian et al.
U.S. Appl. No. 12/057,332, filed Mar. 27, 2008 for Tian et al.
U.S. Appl. No. 12/057,346, filed Mar. 27, 2008 for Tian et al.
U.S. Appl. No. 12/059,610, filed Mar. 31, 2008 for Meng et al.
U.S. Appl. No. 12/141,754, filed Jun. 18, 2008 for Tian et al.
U.S. Appl. No. 12/141,867, filed Jun. 18, 2008 for Tian et al.
Coulombe, S. et al., "Ellipsometric-Scatterometry for sub-01. mm CD measurements", SPIE vol. 3332 (1988) pp. 282-292.
Shifang Li, "Jones-matrix analysis with Pauli matrices: application to ellipsometry", J. Opt. Soc. Am. A; vol. 17, No. 5; May 2000, p. 920-9262.

* cited by examiner

*Primary Examiner* — Roy Punnoose

(57) ABSTRACT

An improved procedure for calibrating the azimuth angle in a metrology module for use in a metrology system that is used for measuring a target on a wafer, and the metrology modules can include oblique Spectroscopic Ellipsometry (SE) and unpolarized or polarized spectroscopic reflectometer devices.

20 Claims, 7 Drawing Sheets

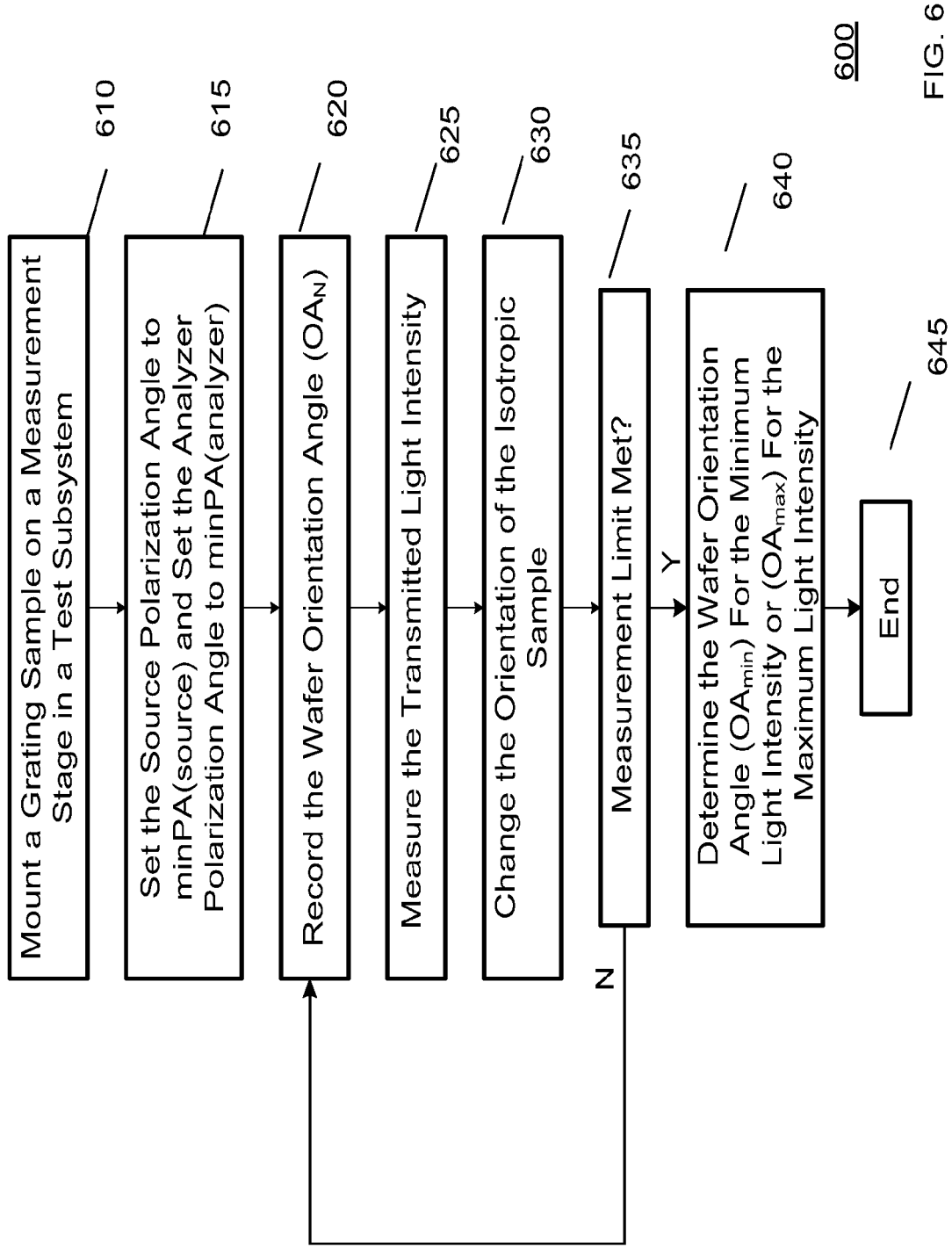

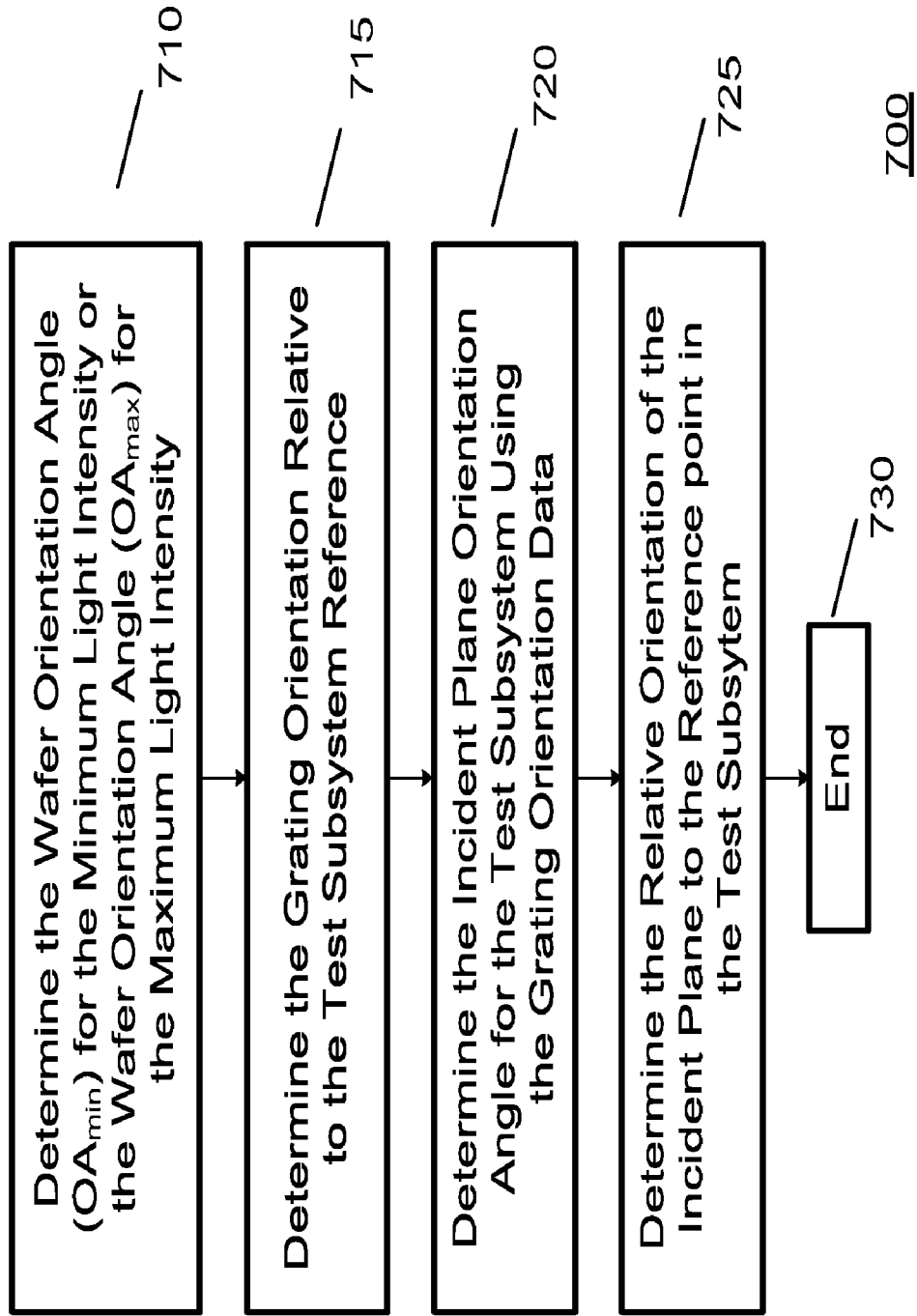

SYSTEM AND METHOD FOR AZIMUTH ANGLE CALIBRATION

BACKGROUND OF THE INVENTION

1. Field of the Invention

The present invention relates to optical metrology, and more particularly to determining the azimuth angle accurately for an oblique Spectroscopic Ellipsometry (SE) or an unpolarized or polarized spectroscopic reflectometer device.

2. Description of the Related Art

In the manufacture of integrated circuits, very thin lines or holes down to 10 nm or sometimes smaller are patterned into photoresist and then often transferred using an etching process into a layer of material below on a silicon wafer. It is extremely important to inspect and control the width and profile (also known as critical dimensions or CDs) of these lines or holes. Traditionally the inspection of CDs that are smaller than the wavelength of visible light has been done using large and expensive scanning electron microscopes. In many cases, however, manufacturers would like to have measurements immediately after the photoresist has been patterned or etched to have tight control of the process before it drifts out of spec. Testing the wafer early during production and controlling the fabrication steps according to the test results helps to keep production costs low and to keep yields high. Ideally, the measurement tool would be integrated into the wafer track that develops the photoresist or integrated into the wafer-etching tool.

In typical stand-alone instruments, the wafer is moved on a stage, while the measurement optics remains stationary. In addition, when the angle of incidence on the wafer is other than zero (e.g. in an ellipsometer), the wafer is preferably oriented so that the plane of incidence is perpendicular to the lines of gratings on the wafer.

One general technique that has promise for integrated CD measurements is Scatterometry. This technique takes advantage of the fact that an array of small lines or holes affects the properties of the light in the zero order that is reflected (and, for transparent samples, transmitted) from such an array. Various measurable properties of the zero-order light will vary depending on the dimensions of the structure on the wafer. Often such parameters are measured versus wavelength, and in some cases, versus angle of incidence on the sample. Normal-incidence spectroscopic reflectometers show particular promise because they can be used with the wafers in any arbitrary orientation. Typically, CD measurements have been made using instruments such as an ellipsometer or reflectometer that were originally designed to measure film thickness. The data from such instruments is usually fed to a processor, which analyzes the measurements, usually by accessing a library of theoretically generated data for a range of array dimensions and film properties near those of the expected dimensions of the sample. The measured data are compared to the library and a best-fit match to a data set in the library is found. The processor then outputs the corresponding dimensions.

Since there are multiple unknown variables that may need to be measured, such as line width, line edge slope, top film thickness, underlying film thickness, or film refractive index, it is desirable that the measurement technique measure as many multiple independent parameters as is practical. It has been shown that there are only 4 independent measurable quantities for a given wavelength and incident condition (angle of incident and azimuth angle). Namely, these 4 measurables are intensity reduction (one independent parameter), and polarization state change (3 independent parameters). Thus, the measurement instrument is improved to measure over a wider wavelength range, and attempts to cover all the four measurable quantities. These techniques are described in U.S. Pat. No. 7,064,829, entitled "Generic Interface for an Optical Metrology System", by Li, et al., issued on Jun. 20, 2006, which is incorporated in its entirety herein by reference. Coulombe et al. ('Ellipsometric-Scatterometry for sub-0.1 mm CD measurements,' SPIE, Vol. 3332, p. 282-292) investigated reflectometry and ellipsometry of line gratings as a function of angle of incidence and azimuth.

Optical metrology involves directing an incident beam at a feature on a wafer, measuring the resulting diffraction signal, and analyzing the measured diffraction signal to determine various characteristics of the feature. In semiconductor manufacturing, optical metrology is typically used for quality assurance. For example, after fabricating a periodic grating in proximity to a semiconductor chip on a semiconductor wafer, an optical metrology system is used to determine the profile of the periodic grating. By determining the profile of the periodic grating, the quality of the fabrication process utilized to form the periodic grating, and by extension the semiconductor chip proximate the periodic grating, can be evaluated.

An integrated CD measurement tool must be both fast and compact, and must not damage the wafer under test. The wafer might rotate, to have a preferred measurement orientation with respect to certain wafer features and to compensate the wafer load tolerance. The wafer may also be loaded into the measurement tool at an arbitrary angle creating further complications for instruments that have a preferred measurement orientation with respect to certain wafer features.

There is a need to increase the tool available time and decrease the maintenance time associated with integrated metrology tools. There is also a need to design integrated metrology tools for measuring CDs and overlay error on periodic structures that are compact and well suited for integration into a wafer process tool.

SUMMARY OF THE INVENTION

The invention presents an apparatus and method to determine the azimuth angle accurately for an oblique Spectroscopic Ellipsometry (SE) or an unpolarized or polarized spectroscopic reflectometer device.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 6 illustrates an exemplary flow diagram procedure used to determine optical incident plane of a pre-alignment metrology module relative to orientation of a structure on a wafer in accordance with embodiments of the invention; and FIG. 7 illustrates an exemplary flow diagram procedure used to determine optical incident plane relative to wafer positioning devices in accordance with embodiments of the invention.

DETAILED DESCRIPTION

Reliability, availability, precision, and accuracy are some of the most important performance parameters for semiconductor equipments in a modern fabrication environment. Many semiconductor manufacturers use optical metrology systems for thin-film and CD measurements that include stand-alone tools, and use off-line applications for process monitoring. As the semiconductor roadmap goes to smaller and smaller nodes, the tightened tolerances associated with the smaller structures become more challenging to obtain and verify using semiconductor off-line process control applications. Thus, integrated metrology tools are required to measure the smaller structures made on the wafer. In addition, the measured data from the integrated metrology tools can be used either to optimize the process tools that are being used to create the structures on the wafer, or to adjust the process tool conditions that are being used to further process the wafer. When the metrology tool is integrated as in-line equipment, much higher reliability and availability are needed because a faulty in-line tool can cause throughput problems in the associated production line.

The present invention provides measurement procedures for Pre-Aligned Metrology Modules to improve tool accuracy and reliability by reducing the time to repair or maintain an in-line metrology tool.

Figure 1:
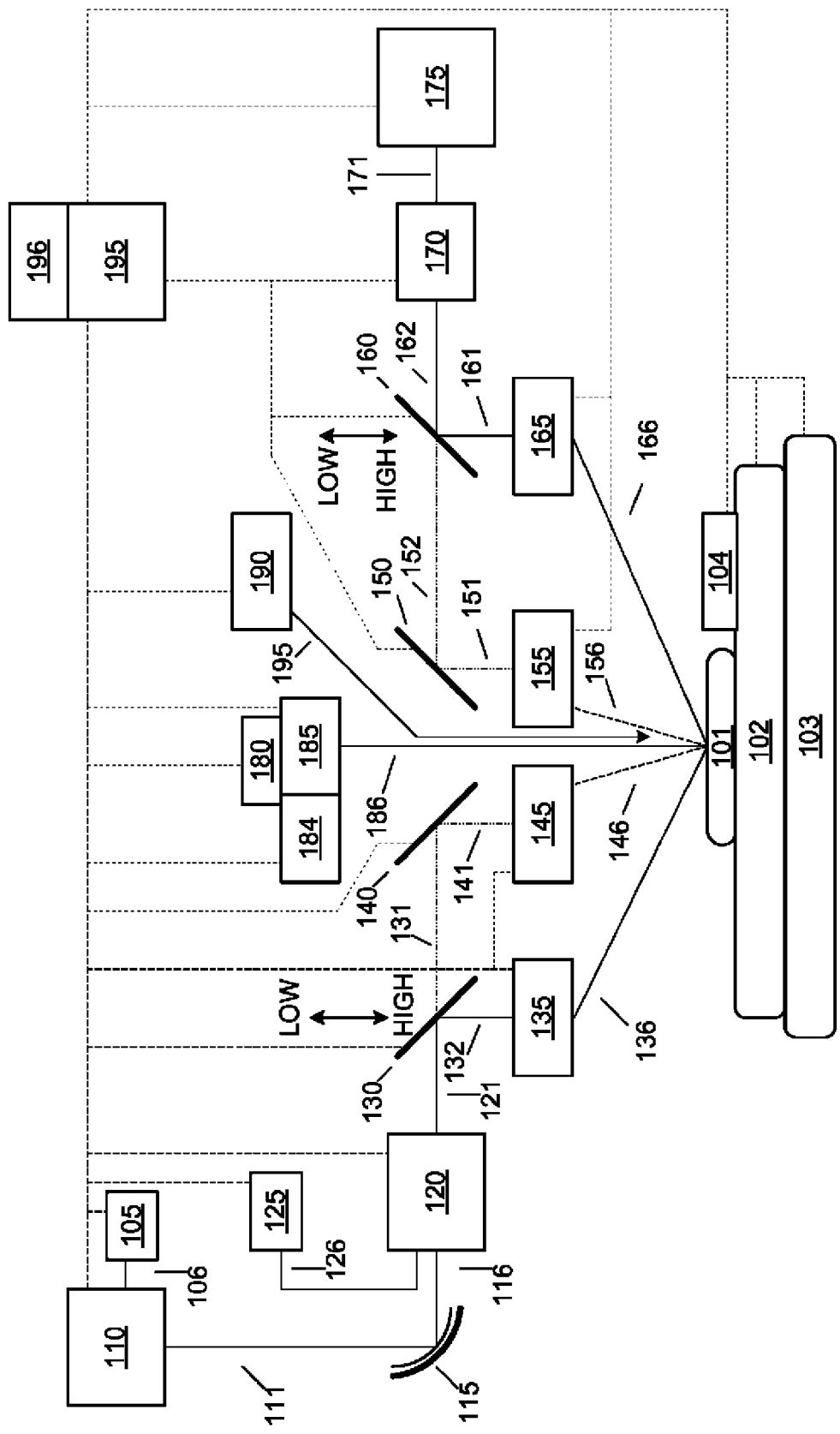
FIG. 1 depicts an exemplary optical metrology system in accordance with embodiments of the invention.

FIG. 1 shows an exemplary block diagram of an optical metrology system in accordance with embodiments of the invention. In the illustrated embodiment, an Integrated optical Metrology Sensor (IMS) 100 can comprise a platform subsystem 103, an alignment subsystem 102 coupled to the platform subsystem 103, an alignment sensor 104 coupled to the alignment subsystem 102, and these subsystems can be configured to align the wafer 101. One or more optical outputs 106 from the lamp subsystem 105 can be transmitted to an illuminator subsystem 110. One or more optical beams 111 can be sent from the illuminator subsystem 110 to a selector subsystem 115. The selector subsystem 115 can provide one or more optical beams 116 to a beam generator subsystem 120. In addition, a reference subsystem 125 can provide one or more reference beams to and/or exchange data with the beam generator subsystem 120 using path 126.

The Integrated Metrology Sensor (IMS) 100 can comprise a first selectable reflection subsystem 130 that can be used to direct one or more outputs 121 from the beam generator subsystem 120 as first outputs 131 when operating in a first mode "HIGH" or as second outputs 132 when operating in a second mode "LOW". When the first selectable reflection subsystem 130 is operating in the first mode "HIGH", one or more of the outputs 132 from the first selectable reflection subsystem 130 can be directed to a first reflection subsystem 140, and one or more outputs 141 from the first reflection subsystem 140 can be directed to a high angle focusing subsystem 145, When the first selectable reflection subsystem 130 is operating in the second mode "LOW", one or more of the outputs 132 from the first selectable reflection subsystem 130 can be directed to a low angle focusing subsystem 135. Alternatively, other modes may be used and other configurations may be used.

When the IMS 100 is operating in the first mode "HIGH", one or more of the incident beams 146 from the high angle focusing subsystem 145 can be directed to the wafer 101. For example, a high angle of incidence can be used. When the IMS 100 is operating in the second mode "LOW", one or more of the incident beams 136 from the low angle focusing subsystem 135 can be directed to the wafer 101. For example, a low angle of incidence can be used. Alternatively, other modes may be used and other configurations may be used.

The IMS 100 can comprise a high angle collection subsystem 155, a low angle collection subsystem 165, a second reflection subsystem 150, and a second selectable reflection subsystem 160.

When the IMS 100 is operating in the first mode "HIGH", one or more of the diffracted beams 156 from the wafer 101 can be directed to the high angle collection subsystem 155. For example, a high angle of incidence can be used. In addition, the high angle collection subsystem 155 can process the diffracted beams 156 obtained from the wafer 101 and high angle collection subsystem 155 can provide outputs 151 to the second reflection subsystem 150, and the second reflection subsystem 150 can provide outputs 152 to the second selectable reflection subsystem 160. When the second selectable reflection subsystem 160 is operating in the first mode "HIGH" the outputs 152 from the second reflection subsystem 150 can be directed to the analyzer subsystem 170. For example, one or more blocking elements can be moved allowing the outputs 152 from the second reflection subsystem 150 to pass through the second selectable reflection subsystem 160 with a minimum amount of loss.

When the IMS 100 is operating in the second mode "LOW", one or more of the low-angle beams from the wafer 101 can be directed to the low angle collection subsystem 165. For example, a low angle of incidence can be used. In addition, the low angle collection subsystem 165 can process the low-angle diffracted beams 166 obtained from the wafer 101 and low angle collection subsystem 165 can provide outputs 161 to the second selectable reflection subsystem 160. When the second selectable reflection subsystem 160 is operating in the second mode "LOW", the outputs 162 from the second selectable reflection subsystem 160 can be directed to the analyzer subsystem 170.

When the IMS 100 is operating in the first mode "HIGH", high incident angle data from the wafer 101 can be analyzed using the analyzer subsystem 170, and when the IMS 100 is operating in the second mode "LOW", low incident angle data from the wafer 101 can be analyzed using the analyzer subsystem 170.

The IMS 100 can include one or more measurement subsystems 175 that can receive inputs 171 from the analyzer subsystem 170. One or more of the measurement subsystems 175 can include one or more spectrometers. For example, the spectrometers can operate from the Deep-Ultra-Violet to the near infrared regions of the spectrum.

The IMS 100 can include one or more camera subsystems 180, one or more illumination, and imaging subsystems 185 coupled to one or more of the camera subsystems 180. In addition, the IMS 100 can also include one or more illuminator subsystems 184 that can be coupled to one or more of the imaging subsystems 185. The imaging subsystem can use optical beams 186 when operating.

In some embodiments, the IMS 100 can include one or more auto-focusing subsystems 190 that can use one or more beams 197 during operation. Alternatively, other focusing techniques may be used.

One or more of the controllers (not shown) in one or more of the subsystems (105, 110, 115, 120, 125, 130, 135, 140, 145, 150, 155, 160, 165, 170, 175, 180, 185 and 190) can be used when performing real-time or non-real-time procedures. A controller can receive real-time or non-real-time data to update subsystem, processing element, process, recipe, profile, image, pattern, and/or model data. One or more of the subsystems (105, 110, 115, 120, 125, 130, 135, 140, 145, 150, 155, 160, 165, 170, 175, 180, 185 and 190) can exchange data using one or more Semiconductor Equipment Communications Standard (SECS) messages, can read and/or remove information, can feed forward, and/or can feedback the information, and/or can send information as a SECS message.

Those skilled in the art will recognize that one or more of the subsystems (105, 110, 115, 120, 125, 130, 135, 140, 145, 150, 155, 160, 165, 170, 175, 180, 185, and 190) can include computers and memory components (not shown) as required. For example, the memory components (not shown) can be used for storing information and instructions to be executed by computers (not shown) and may be used for storing temporary variables or other intermediate information during the execution of instructions by the various computers/processors in the IMS 100. One or more of the subsystems (105, 110, 115, 120, 125, 130, 135, 140, 145, 150, 155, 160, 165, 170, 175, 180, 185, and 190) can include the means for reading data and/or instructions from a computer readable medium and can comprise the means for writing data and/or instructions to a computer readable medium.

The IMS 100 can perform a portion of or all of the processing steps of the invention in response to the computers/processors in the processing system executing one or more sequences of one or more instructions contained in a memory and/or received using a computer-readable medium. Such instructions may be received from another computer, a computer readable medium, or a network connection. In addition, one or more of the subsystems (105, 110, 115, 120, 125, 130, 135, 140, 145, 150, 155, 160, 165, 170, 175, 180, 185, and 190) can comprise control applications, Graphical User Interface (GUI) components, and/or database components. For example, the control applications can include Advanced Process Control (APC) applications, Fault Detection and Classification (FDC), and/or Run-to-Run (R2R) applications. In some embodiments, APC applications, FDC applications, and/or R2R applications can be performed using multi-angle metrology procedures.

In some embodiments, the IMS 100 can include Optical Digital Profilometry (ODP) elements (not shown), and ODP elements/systems are available from Timbre Technologies Inc. (a TEL company). Alternatively, other data analysis elements for the metrology systems may be used. For example, ODP techniques can be used to obtain real-time data that can include critical dimension (CD) data, gate structure data, thickness data, and the wavelength ranges for the ODP data can range from less than approximately 195 nm to greater than approximately 900 nm. Exemplary ODP elements can include Optical Digital Profilometry Profiler Library elements, Profiler Application Server (PAS) elements, and other ODP Profiler Software elements. The ODP Profiler Library elements can comprise application specific database elements of optical spectra and its corresponding semiconductor profiles, critical dimensions (CDs), and film thicknesses. The PAS elements can comprise at least one computer that connects with optical hardware and computer network. The PAS elements can be configured to provide the data communication, ODP library operation, results generation, results analysis, and results output. The ODP Profiler Software elements can include the software installed on PAS elements to manage measurement recipe, ODP Profiler library elements, ODP Profiler data, ODP Profiler search/match results, ODP Profiler calculation/analysis results, data communication, and PAS interface to various metrology elements and computer network.

The IMS 100 can use polarizing reflectometry, spectroscopic ellipsometry, spectroscopic reflectometry, or other optical measurement techniques to measure accurate feature profiles, accurate CDs, and multiple layer film thickness of a wafer. The integrated data process can be executed as an integrated data analyzer in an integrated group of subsystems. In addition, the integrated group that consists of IMS 100 and data analyzer (ODP) into a process tool eliminates the need to break the wafer for performing the analyses or waiting for long periods for data from external systems. iODP techniques can be integrated with Tokyo Electron Limited (TEL) processing systems and/or lithography systems and etch systems to provide real-time process monitoring and control.

An exemplary ODP is described in U.S. Pat. No. 6,913,900, entitled GENERATION OF A LIBRARY OF PERIODIC GRATING DIFFRACTION SIGNAL, by Niu, et al., issued on Sep. 13, 2005, and is incorporated in its entirety herein by reference.

Simulated diffraction signals with ODP can be generated by applying Maxwell's equations and using a numerical analysis technique to solve Maxwell's equations. For example, various numerical analysis techniques, including variations of rigorous coupled wave analysis (RCWA), can be used with multi-layer structures. For a more detail description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

An alternative procedure for generating a library of simulated-diffraction signals can include using a machine learning system (MLS). Prior to generating the library of simulated-diffraction signals, the MLS is trained using known input and output data. For example, the MLS may be trained with a subset of the D-P library data. In one exemplary embodiment, simulated diffraction signals can be generated using a MLS employing a machine learning algorithm, such as back-propagation, radial basis function, support vector, kernel regression, and the like. For a more detailed description of machine learning systems and algorithms, see "U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In various embodiments, one or more of the subsystems (105, 110, 115, 120, 125, 130, 135, 140, 145, 150, 155, 160, 165, 170, 175, 180, 185, and 190) can perform evaluation procedures, inspection procedures, temperature control procedures, measurement procedures, alignment procedures, verification procedures, and/or storage procedures on one or more wafers. For example, wafer data that can include wafer temperature, wafer thickness, wafer curvature, layer thickness, wafer uniformity, pattern data, damage data, or particle data, or any combination thereof. In addition, controller 195 can determine if the wafer has been processed correctly or if a rework procedure is required.

The IMS 100 data can include measured, predicted, and/or simulated data associated with structures, and the data can be stored using processing, wafer, lot, recipe, site, or wafer location data. the data can include variables associated with patterned structure profile, metrology device type and associated variables, and ranges used for the variables floated in the modeling and values of variables that were fixed in the modeling. The library data may include fixed and/or variable profile parameters (such as CD, sidewall angle, refractive index (n) data and extinction coefficient (k) data), and/or metrology device parameters (such as wavelengths, angle of incidence, and/or azimuth angle). For example, context and/or identification information such as sensor ID, site ID, wafer ID, slot ID, lot ID, recipe, state, and patterned structure ID may be used for organizing and indexing data.

Controller 195 can include coupling means 196 that can be used to couple the IMS 100 to other systems in a factory environment. In some examples, controller 195 may be configured to use factory level intervention and/or judgment rules to determine which processes are monitored and which data can be used. In addition, factory level intervention and/or judgment rules can be used to determine how to manage the data when a process can be changed, paused, and/or stopped. In addition, controller 195 can provide configuration information and update information.

Figure 2:
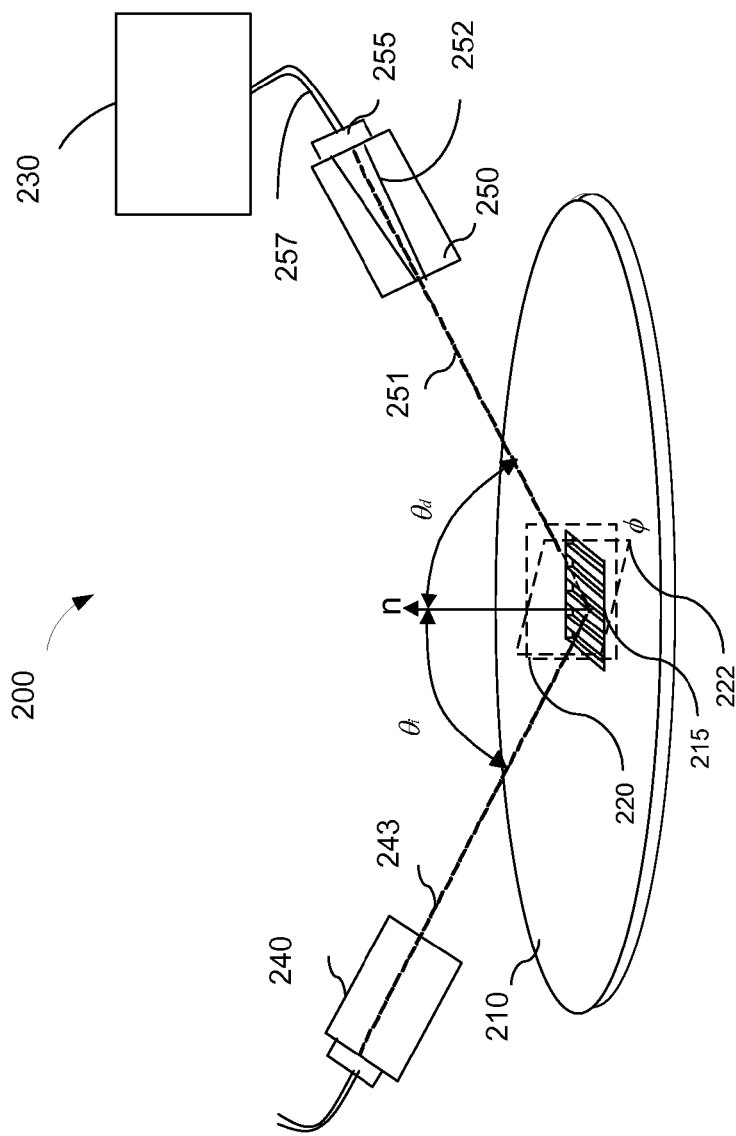
FIG. 2 depicts another exemplary optical metrology system in accordance with embodiments of the invention.

FIG. 2 depicts an exemplary optical metrology system in accordance with embodiments of the invention. In the illustrated embodiment, an optical metrology system 200 is shown that can be used to examine and analyze a 3-D or 2-D structure formed on a semiconductor wafer. Alternatively, other configurations may be used. The illustrated optical metrology system 200 can be used to determine the profile of a target structure 215 formed on wafer 210. The target structure 215 can be formed in test areas on wafer 210, such as adjacent to a device formed on wafer 210. In other embodiments, target structure 215 can be formed in an area of the device that does not interfere with the operation of the device or along scribe lines on wafer 210.

The illustrated optical metrology system 200 can include a photometric device with a beam source 240 and a beam receiver 250. Target structure 215 can be illuminated by an incident beam 243 from beam source 240. In the illustrated exemplary embodiment, incident beam 243 is directed onto target structure 215 at an incidence angle $\theta_i$ with respect to normal $\vec{n}$ (i.e., the angle between the direction of the beam and normal $\vec{n}$ of the target structure 215) and an azimuth angle $\phi$ (i.e., the angle between the plane of incidence beam 243 (incidence plane 222, formed by the incident beam 243 and the normal $\vec{n}$ and the direction of the periodicity of target structure 215 (grating plane 220, the plane perpendicular to the grooves of the grating). Measurement beam 251 leaves at a diffracted angle of $\theta_d$ with respect to normal $\vec{n}$ and can be received by beam receiver 250. Typically, the zero-th order diffraction beam is collected and detected. For zero-th order beam, $\theta_d = \theta_i$, the diffracted beam is in the incident plane. The photometric sensor 255 in the beam receiver can convert the measurement light intensity of measurement beam 251 into measurement electrical signal, and further digitized into data 257 for analysis. In addition, the measurement beam 251 can have a beam width 252 at the beam sensor 255. Beam receiver 250 measures the diffracted beam 251 as a measured diffraction signal, which can include reflectance (R), polarization state changes ($\Theta_x$, $\Theta_y$, $\Theta_z$), zero order cross polarization efficiencies/amplitudes, tan ($\Psi$), cos($\Delta$), ($\Psi$, $\Delta$), Fourier coefficients, and the like.

Optical metrology system 200 also includes one or more controller/servers 230 configured to receive the measured diffraction signal and analyze the measured diffraction signal. As described below, a target structure 215 can then be determined using various linear or non-linear profile extraction techniques, such as a library-based process, a regression-based process; and the like. For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety. For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, and filed on Aug. 6, 2001, which is incorporated herein by reference in its entirety. For a more detailed description of a machine learning system, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

However, when performing optical metrology on a structure, measurement errors may occur if the structure and the incident beam are not properly aligned azimuthally. In particular, cross polarization components of the diffracted beam may complicate the signal measurements, and cause errors between the measured signals and the analysis model used in optical metrology.

For example, for a typical optical metrology system with polarized photometric configurations, beam receiver 250 data can be expressed as reflectance R and polarization state changes ($\Theta_x$, $\Theta_y$, $\Theta_z$), or ellipsometer parameters ($\Psi$, $\Delta$) [see reference Jones-matrix analysis with Pauli matrices: application to ellipsometry, Shifang Li, J. Opt. Soc. Am. A; Vol. 17, No. 5; May 2000, p 920-926]. Thus, the effective ellipsometer parameter:

$$\tilde{r}_s \equiv \frac{E_s^{out}}{E_s^{in}} = \frac{E_0 \cdot (r_{ss} \cos P + r_{sp} \sin P)}{E_0 \cdot \cos P}$$

$$\tilde{r}_p \equiv \frac{E_p^{out}}{E_p^{in}} = \frac{E_0 \cdot (r_{pp} \sin P + r_{ps} \cos P)}{E_0 \cdot \sin P}$$

$$\tilde{\rho} \equiv \tan\Psi e^{i\Delta} \equiv \frac{\tilde{r}_p}{\tilde{r}_s} = \frac{r_{pp} \sin P \cdot \cos P + r_{ps} \cos^2 P}{r_{ss} \cos P \cdot \sin P + r_{sp} \sin^2 P}$$

where $E_p$ is the component of diffracted electric field parallel to the plane of incidence, $E_s$ is the component of diffracted electric field perpendicular to the plane of incidence, P is the polarization angle, and $r_{pp}$, $r_{sp}$, $r_{ps}$, and $r_{ss}$ are the components of Jones matrix for diffraction of the feature on wafer. When the measurements are performed with the grating mounted conically, all four polarized reflectance terms $r_{pp}$, $r_{sp}$, $r_{ps}$, and $r_{ss}$ are non-zero, and this will require extra computation to simulate the diffraction signal. It is preferred to align the grating in the measurement at a non-conically mounted condition, so that the cross polarization terms vanish, and the measurement and data analysis can be simplified and performed with higher accuracy. The invention here is to analysis the cross polarization terms to determine accurately the incident plane relative to the grooves of the grating.

Note that when P is in the range from 20° to 70°, the cross-polarization terms, $r_{sp}$, $r_{ps}$ are strongly interfacing with the in-polarization terms $r_{ss}$ or $r_{pp}$. The cross polarization terms, $r_{sp}$, $r_{ps}$, are typically small in quantity relative to the in-polarization terms, $r_{ss}$, $r_{pp}$, especially when the azimuthal angle is varied across zero, and a maximum or a minimum does not occur when the azimuthal angle is varied across zero degrees. Thus, it is very difficult to measure the cross polarization terms, $r_{sp}$, $r_{ps}$. However, when P is 0° or 90°, one of the field components of the in-polarization terms, $r_{ss}$ or $r_{pp}$, vanishes, leaving the field component due to cross-polarization terms, $r_{sp}$, $r_{ps}$, alone either as an S or as a P field component of the diffracted beam. Further, note that, when the azimuthal angle is 0° or 90° also, the field component due to cross polarization term vanishes too, a null signal in the detected beam is expected under these conditions. Thus, in the present exemplary embodiment, nulling the signal detected by setting P=0° or 90° and varying the azimuthal angle, the azimuthal angle can be determined as 0° or 90°. The procedure present here is independent of the characterization of the grating structure. This gives a great flexibility to the measurement, and at the same time, the calibration results can be checked by using additional gratings after the calibration.

Optical metrology typically includes comparing a measured diffraction signal to a simulated diffraction signal, where the simulated diffraction signal is associated with a hypothetical profile of the structure. If the measured diffraction signal matches the simulated diffraction signal or when the difference of the measured diffraction signal and the simulated diffraction signal is within a preset or matching criterion, the hypothetical profile associated with the matching simulated diffraction signal is presumed to represent the actual profile of the structure.

In generating the simulated diffraction signal, an azimuth angle is assumed. Differences between the azimuth angle assumed in generating the simulated diffraction signal (i.e., the assumed azimuth angle) and the azimuth angle used in obtaining the measured diffraction signal (i.e., the actual azimuth angle) may produce erroneous results. For example, due to the difference in the assumed and azimuth angles, the hypothetical profile associated with the matching simulated diffraction signal may not be representative of the actual profile, and the goodness of fit (GOF) is typically worse. This leads to another method to determine the azimuth angle by measuring the grating with scanning azimuthal angle and monitoring the GOF variation, as described below.

During some procedures, measurement scans can be performed and the data obtained during a measurement scan can be used to determine a zero azimuth position, or a beam position, where the cross polarization terms are zero, to detect azimuthal misalignment between the azimuth angle used in obtaining the measured diffraction signal with the azimuth angle used in generating the simulated diffraction signal, and to detect incident angle misalignment between the incident angle used in obtaining the measured diffraction signal with the incident angle used in generating the simulated diffraction signal. As described in more detail below, the signal measurements, and more particularly the cross polarization terms of the signal measurements, are zero at certain azimuth angles.

In other exemplary embodiment, the cross polarization can be measurement and determined accurately by presetting P close to 0° or 90°. For example, when using an ellipsometer with polarization angle P of ~0° or ~90°, the effective ellipsometer signal can be expressed as:

$$\tilde{\rho} = \tan\Psi e^{i\Delta} \approx \frac{r_{ps}}{r_{ss}} \cdot \frac{1}{\tan P} (P \approx 0)$$

or $$\tilde{\rho} = \tan\Psi e^{i\Delta} \approx \frac{r_{pp}}{r_{sp}} \cdot \frac{1}{\tan P} (P \approx 90°)$$

If only the amplitude terms are considered, the angle $\Psi$ can be expressed as:

$$\Psi = \arctan\frac{|r_{ps}|/\tan P}{|r_{ss}|} (P \approx 0)$$

or $$\Psi = \arctan\frac{|r_{pp}|}{|r_{sp}| \cdot \tan P} (P \approx 90°)$$

As shown above the measurement sensitivity to $|r_{ps}|$ is magnified by factor of 1/tan(P) at P~0°, and sensitivity to $|r_{sp}|$ is magnified by factor of tan(P) at P~90°. The signal measurements, and more particularly the cross polarization terms of the signal measurements $r_{sp}$, $r_{ps}$, can be zero when azimuth angle ϕ is 0°, 90°, 180°, and 270°.

Thus, in the present exemplary application, the simulated diffraction signals used in optical metrology of a grating array are generated using an azimuth angle corresponding to when the signal measurements, and more particularly the cross polarization terms of the signal measurement, are zero when azimuth angle ϕ is 0°, 45°, 90°, 135°, 180°, 225°, 270°, and 315°. Before obtaining the measured diffraction signal from a grating array to compare to a simulated diffraction signal, one or more measurement scans of the target structure can be performed. In some examples, the signal measurements obtained from an azimuthal scan can then be used to detect the amount of misalignment of the azimuth angle. In other examples, the signal measurements obtained from an incident angle or diffraction angle scan can then be used to detect the amount of misalignment of the incident angle. These misalignments can then be corrected during pre-alignment procedures.

Figure 3:
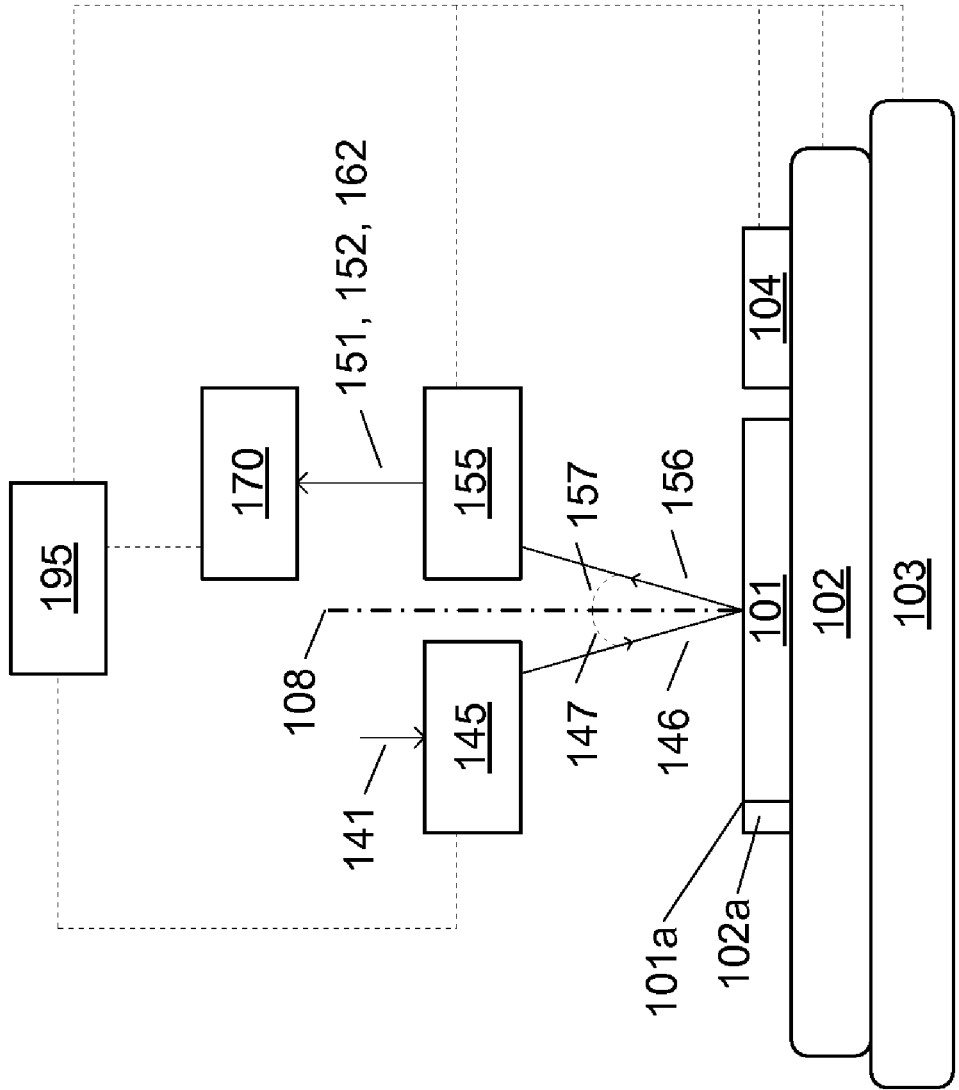
FIG. 3 illustrates a simplified block diagram of a first configuration of a first portion of the Integrated Metrology Sensor (IMS) in accordance with embodiments of the invention.

FIG. 3 illustrates a simplified block diagram of a first configuration of a first portion of the IMS 100 in accordance with embodiments of the invention. In the illustrated embodiment, a first configuration 300 of the IMS 100 is shown, but this is not required for the invention. Alternatively, other configurations may be used.

The first configuration 300 can include a platform subsystem 103, an alignment subsystem 102 coupled to the platform subsystem 103, an alignment sensor 104 coupled to the alignment subsystem 102, and these subsystems can be configured to align the wafer 101. The IMS 100 can include an alignment subsystem 102 that can be coupled to a platform subsystem 103. The position and orientation for the platform subsystem 103 can be used to determine the position and orientation of the alignment subsystem 102, and the wafer 101. In some configurations, the alignment subsystem 102 can be used to move the wafer 101 laterally, vertically, and/or rotationally, and one or more alignment sensors 104 can be used to determine the position and orientation of the alignment subsystem 102 and the wafer 101. In some examples, the alignment subsystem 102 can include an alignment element 102a that can be used to establish a reference point for orienting a wafer notch 101a during alignment and/or positioning procedures. In other examples, the position and/or orientation of the wafer notch can be determined differently.

The first configuration 300 can include a high angle focusing subsystem 145. When the IMS 100 is operating in the first mode "HIGH", one or more of the input beams 141 can be provided to the high angle focusing subsystem 145, and the high angle focusing subsystem 145 can create one or more of incident beams 146 that can be directed to the wafer 101. For example, the incident beams 146 can have a high angle of incidence 147, and the high angle of incidence 147 can vary from 10 degrees to 50 degrees when measured relative to a normal vector 108.

The first configuration 300 can include one or more high angle collection subsystems 155. When the IMS 100 is operating in the first mode "HIGH", one or more of the diffracted beams 156 from the wafer 101 can be directed to the high angle collection subsystem 155. For example, the diffracted beams 156 can have a high diffraction angle 157, and the high diffraction angle 157 can vary from 10 degrees to 50 degrees when measured relative to a normal vector 108.

In addition, the high angle collection subsystem 155 can process the diffracted beams 156 obtained from the wafer 101 and high angle collection subsystem 155 can provide optical outputs 151. In some configurations, the optical outputs 151 can be directed to an analyzer subsystem 170 using paths (152 and 162, FIG. 1). Alternatively, other configurations may be used. For example, when the IMS 100 is operating in the first mode "HIGH" the outputs 151 can be directed to the analyzer subsystem 170.

During some procedures, the polarization angle of the incident beam 146 relative to the incident plane can be determined for the IMS 100. For example, and an isotropic sample 101 (e.g. a thin film wafer) can be positioned on the alignment subsystem 102 in the test chamber. The wavelength and/or the polarization angle associated with the analyzer subsystem 170 can be adjusted to measure a diffracted beam 156. For example, a measurable transmission value of the incident beam can be established for one or more wavelengths. Next, the polarization angle of the incident beam 146 can be adjusted to a known value, the polarization angle associated with the analyzer subsystem 170 can be adjusted to find a minimum transmission value for this wavelength, and the transmission value for this wavelength and polarization angle can be recorded. Then, the polarization angle of the incident beam 146 can be changed by a known quantity, the polarization angle associated with the analyzer subsystem 170 can be changed again to find a new minimum transmission value for the system, and the value for new polarization angle, the new minimum transmission value for the new polarization angle setting, and the polarization angle associated with the analyzer subsystem 170. For example, these steps can be repeated a number times to find the functional relationship that links the minimum transmission with polarization angle setting. This functional relationship will show a minimum at a polarization angle, and that angle corresponds to the polarization angle that is in phase or 90 degrees out of phase with the incident plane.

When an anisotropic wafer 101 (such as with a grating) is illuminated obliquely and conically, with the incidence angle $\theta_i$ is not equal to zero degrees and the azimuthal angle $\phi$ is not equal to zero degrees. Zero-order cross polarization measurements can be obtained, and beam and angle measurements can be obtained based on the zero-order cross polarization measurements. A zero azimuth position can be determined during the alignment procedures. The cross polarization components are zero at the zero azimuth position. Misalignment of the beams (146 and 156) can be detected during the alignment procedures using one or more wavelengths.

In other embodiments, detecting misalignment can include: generating a simulated diffraction signal using an assumed azimuth position; comparing the simulated diffraction signal to the measured diffraction signal while floating the azimuth angle; and when the simulated diffraction signal and the measured diffraction signal match within a matching criterion, detecting misalignment of the azimuth angle as the assumed azimuth position that best fits the measured data. For example, the high angle focusing subsystem 145 and/or the analyzer subsystem 170 can use first polarization angle settings, such as 90 degrees/0 degrees, to obtain a first zero-order cross polarization measurement, and the high angle focusing subsystem 145 and/or the analyzer subsystem 170 can use second polarization angle settings that are rotated 90 degrees from the first polarization angle settings, such as 0 degrees/90 degrees, to obtain a second zero-order cross polarization measurement.

In additional embodiments, the analyzer subsystem 170 may include a split-pupil lens (not shown) that can be used to obtain zero-order cross polarization measurements without having to switch the angular settings, and s-p polarization measurement and a p-s polarization measurement can be obtained concurrently.

Figure 4:
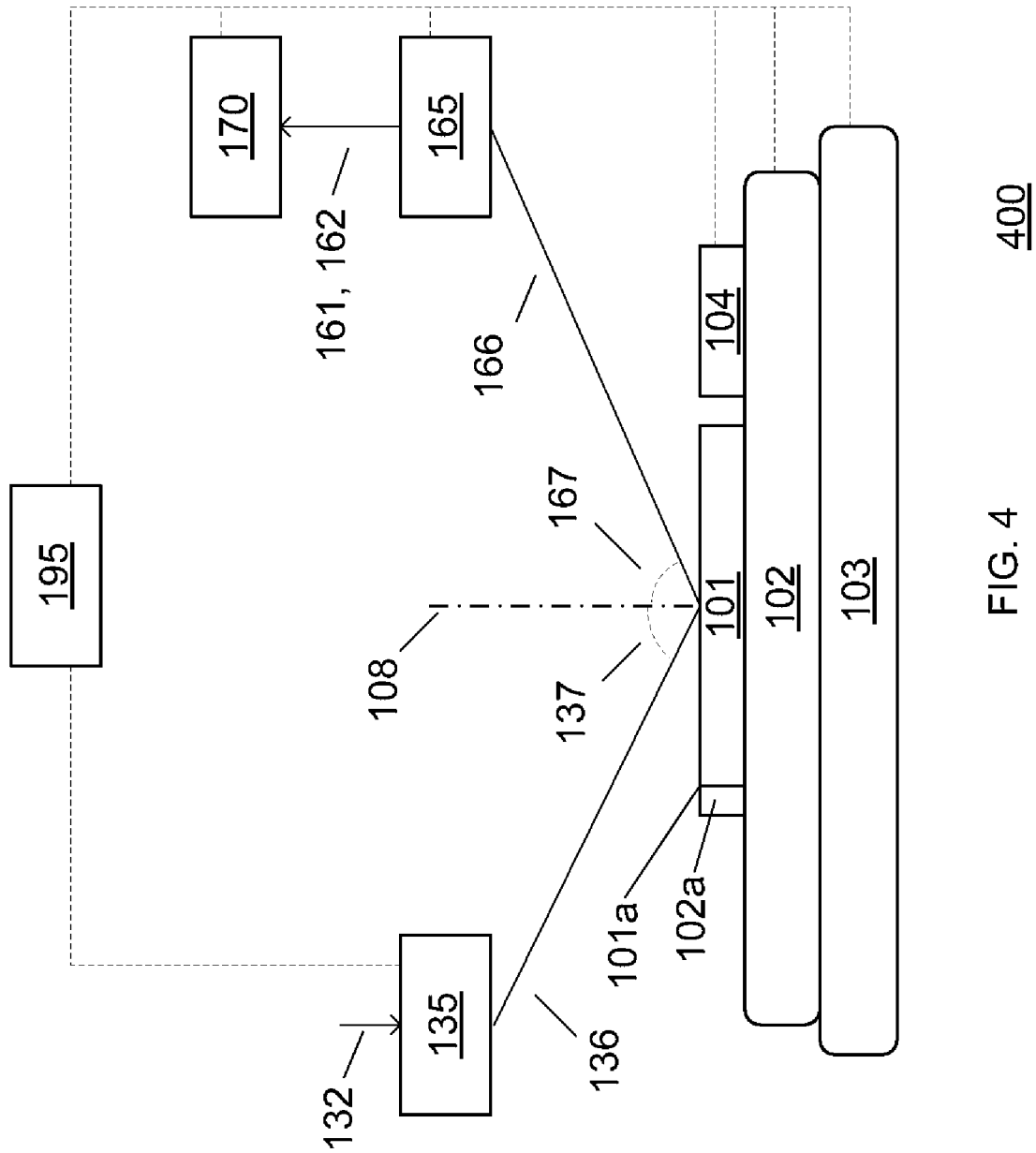
FIG. 4 illustrates a simplified block diagram of a second configuration of a second portion of the Integrated Metrology Sensor (IMS) in accordance with embodiments of the invention.

FIG. 4 illustrates a simplified block diagram of a second configuration of a second portion of the IMS 100 in accordance with embodiments of the invention. In the illustrated embodiment, a second configuration 400 of the IMS 100 is shown, but this is not required for the invention. Alternatively, other configurations may be used.

The second configuration 400 can include a platform subsystem 103, an alignment subsystem 102 coupled to the platform subsystem 103, an alignment sensor 104 coupled to the alignment subsystem 102, and these subsystems can be configured to align the wafer 101. The IMS 100 can include an alignment subsystem 102 that can be coupled to a platform subsystem 103. The position and orientation for the platform subsystem 103 can be used to determine the position and orientation of the alignment subsystem 102, and the wafer 101. In some configurations, the alignment subsystem 102 can be used to move the wafer 101 laterally, vertically, and/or rotationally, and one or more alignment sensors 104 can be used to determine the position and orientation of the alignment subsystem 102 and the wafer 101. In some examples, the alignment subsystem 102 can include an alignment element 102a that can be used to establish a reference point for orienting a wafer notch 101a during alignment and/or positioning procedures. In other examples, the position and/or orientation of the wafer notch can be determined differently.

The second configuration 400 can include a low-angle focusing subsystem 135. When the IMS 100 is operating in the second mode "LOW", one or more of the output beams 132 can be provided to the low-angle focusing subsystem 135, and the low-angle focusing subsystem 135 can create one or more low-angle incident beams 136 that can be directed to the wafer 101. For example, the low-angle incident beams 136 can have a low angle of incidence 137 and the low angle of incidence 137 can vary from 50 degrees to 80 degrees when measured relative to a normal vector 108.

The second configuration 400 can include one or more low-angle collection subsystems 165. When the IMS 100 is operating in the second mode "LOW", one or more of the low-angle diffracted beams 166 from the wafer 101 can be directed to the low-angle collection subsystem 165. For example, the low-angle diffracted beams 166 can have a low diffraction angle 167, and the low diffraction angle 167 can vary from 50 degrees to 80 degrees when measured relative to a normal vector 108.

In addition, the low-angle collection subsystem 165 can process the low-angle diffracted beams 166 obtained from the wafer 101 and low-angle collection subsystem 165 can provide optical outputs 161. In some configurations, the optical outputs 161 can be directed to an analyzer subsystem 170 using path (162, FIG. 1). Alternatively, other configurations may be used. For example, when the IMS 100 is operating in the second mode "LOW", the optical outputs 161 can be directed to the analyzer subsystem 170.

During some procedures, the polarization angle of the incident beam 136 relative to the incident plane can be determined for the IMS 100. For example, using an isotropic sample 101 (e.g. a thin film wafer) can be positioned on the alignment subsystem 102. The wavelength and/or the polarization angle associated with the analyzer subsystem 170 can be adjusted to measure a low-angle diffracted beam 166. For example, a measurable transmission value can be established for one or more wavelengths. Next, the polarization angle of the incident beam 136 can be adjusted to a known value, the polarization angle associated with the analyzer subsystem 170 can be adjusted to find a minimum transmission value for this wavelength, and the transmission value for this wavelength and polarization angle can be recorded. Then, the polarization angle of the incident beam 136 can be changed by a know quantity, the polarization angle associated with the analyzer subsystem 170 can be changed again to find a new minimum transmission value for the system, and the value for new polarization angle, the new minimum transmission value for the new polarization angle setting, and the polarization angle associated with the analyzer subsystem 170. For example, these steps can be repeated a number times to find the functional relationship that links the minimum transmission with polarization angle setting. This functional relationship will show a minimum at a polarization angle, and that angle corresponds to the polarization angle that is 0 or 90 degrees with the incident plane.

When an anisotropic wafer (such as a grating) 101 is illuminated obliquely and conically, the incidence angle $\theta_i$ is not equal to zero degrees and the azimuthal angle $\phi$ is not equal to zero degrees. Zero-order cross polarization measurements can be obtained, and beam and angle measurements can be obtained based on the zero-order cross polarization measurements. The cross polarization components are zero at the zero azimuth position. By nulling the cross polarization, the incident beam azimuth position is aligned to zero. Misalignment of the beams (146 and 156) can be detected during the alignment procedures using one or more wavelengths.

In other embodiments, detecting misalignment can include: generating a simulated diffraction signal using an assumed zero azimuth position; comparing the simulated diffraction signal to the measured diffraction signal; and when the simulated diffraction signal and the measured diffraction signal match within a matching criterion, detecting mismatch of the measured signal differs from the simulated signal assumed zero azimuth position. Scan the azimuth angle in measurement, the azimuth angle that corresponds to the measurement signal that has minimum mismatch is the zero azimuth position. This procedure can be performed with 0 degree or 90 degree of polarizer angle. For example, the low-angle focusing subsystem 135 and/or the analyzer subsystem 170 can use first polarization angle settings, such as 90 degrees/0 degrees, to obtain a first zero-order cross polarization measurement, and the low-angle focusing subsystem 135 and/or the analyzer subsystem 170 can use second polarization angle settings that are rotated 90 degrees from the first polarization angle settings, such as 0 degrees/90 degrees, to obtain a second zero-order cross polarization measurement.

Figure 5:
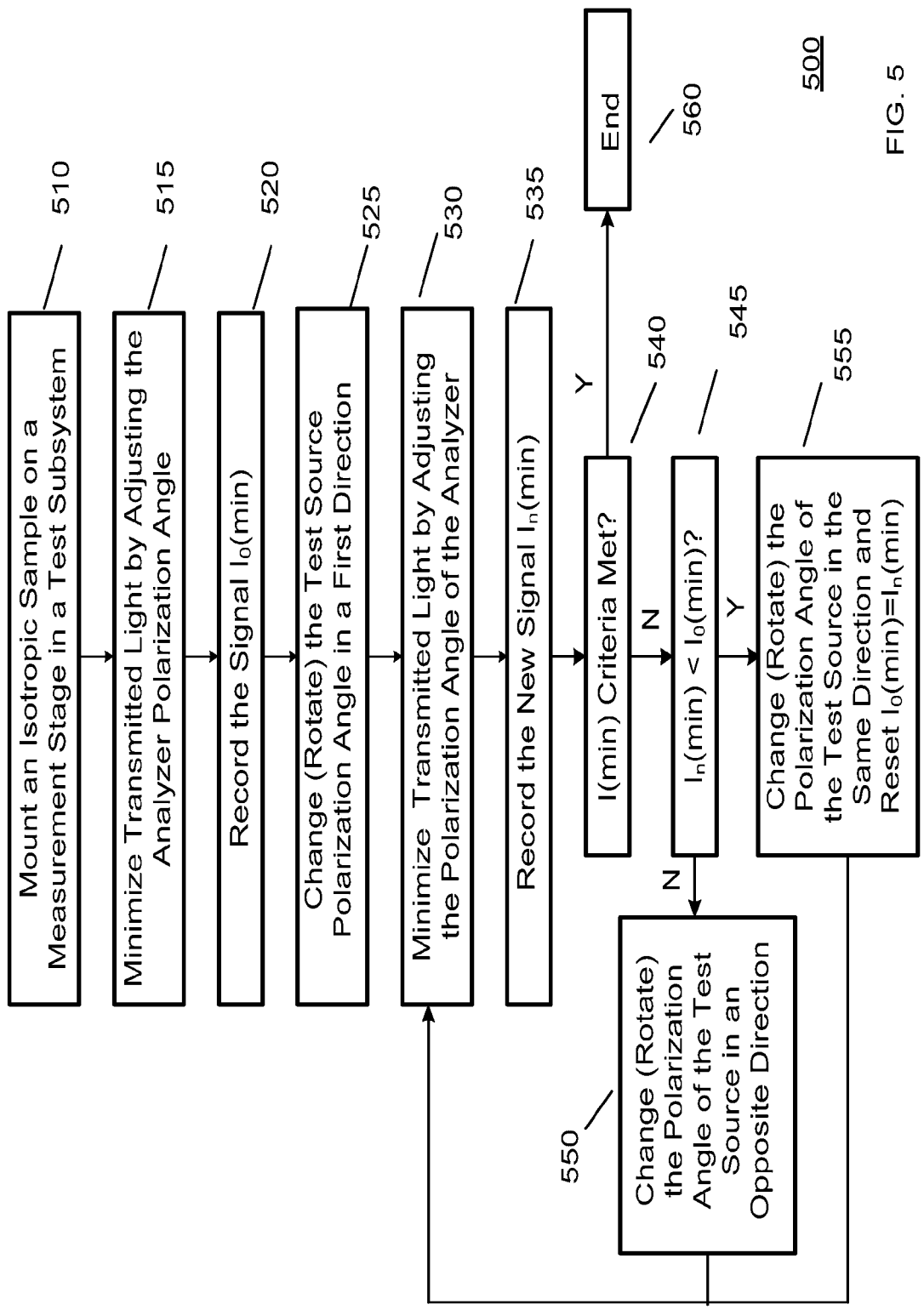
FIG. 5 illustrates an exemplary flow diagram procedure used to determine polarizer and analysis angle relative to optical incident plane of a metrology module in accordance with embodiments of the invention.

FIG. 5 illustrates an exemplary flow diagram procedure used to determine polarization angles relative to optical incident plane of IMS 100 in accordance with embodiments of the invention. For example, the pre-alignment procedure for an IMS 100 can be performed using different sets of subsystems.

In 510, an isotropic sample 101 (e.g. a thin film wafer) can be positioned on the alignment subsystem 102 in the IMS 100. When a wafer is positioned on the alignment subsystem 102, an alignment element 102*a* and a wafer notch 101*a* may be used to align the wafer on the alignment subsystem 102. In addition, the alignment subsystem 102 can be adjusted to locate the diffracted beams (156, 166) and determine the diffraction angles (157, 167).

In 515, a first (reference) minimum transmission value $I_0(\text{min})$ can be determined, and the amount of transmitted light, as measured by the analyzer subsystem 170, can be minimized by adjusting the analyzer polarization angle associated with the analyzer. For example, the polarization angles associated with the incident beams (136, 146) can be adjusted to a known value using the focusing subsystems (135, 145), and the polarization angle associated with the analyzer subsystem 170 can be adjusted in a range from approximately 0 degrees to approximately 180 degrees to find a minimum transmission value of the diffracted beam, as measured by the analyzer subsystem 170.

In some embodiments, one or more of the subsystems (105, 110, 115, 120, 130, 140, and 195) can be used to establish and/or change the beams (132 in FIG. 4, 141 in FIG. 3). The controller 195 can be used to establish and/or change one or more of the optical outputs 106 from the lamp subsystem 105 or the reference subsystem 125. Alternatively, an optical test source can be used In 520, the transmission value $I_0(\text{min})$ for this polarization angle setting can be stored and can be used as a reference value. The minimum polarization angle for the IMS 100 and the minimum polarization angle for the analyzer subsystem 170 can be stored, plotted, and/or displayed. In addition, the maximum transmission value $I_0(\text{max})$, maximum polarization angle for the IMS 100, and/or the maximum polarization angle for the analyzer subsystem 170 can be stored, plotted, and/or displayed.

In 525, the polarization angle associated with the IMS 100 can be changed by a known quantity (<five degrees) in a first direction. For example, the polarization angle associated with the beams (132, 141) can be changed.

In 530, a new minimum transmission value $I_N(\text{min})$ can be determined, and the amount of transmitted light associated with the new polarization angle can be minimized by adjusting the polarization angle associated with the analyzer subsystem 170. A new analyzer polarization angle can be determined that provides a new minimum transmission value $I_N(\text{min})$ as measured by the analyzer subsystem 170. For example, the polarization angle associated with the analyzer subsystem 170 can be changed from approximately 0 degrees to approximately 180 degrees during the measurements. Alternatively, other configurations may be used.

In 535, the new minimum transmission value $I_N(\text{min})$, the new minimum polarization angle, and the new minimum polarization angle associated with analyzer subsystem 170 can be stored and can be used to create a graph or determine a functional relationship between the minimum transmission values and the polarization angle for the IMS 100. Alternatively, the maximum transmission value $I_0(\text{max})$, maximum polarization angle, and/or the maximum polarization angle value associated with analyzer subsystem 170 can be stored, plotted, and/or displayed.

In 540, a query can be performed to determine if an I(min) criteria has been met. When the I(min) criteria have been met, procedure 500 can branch to step 560 and end. When the I(min) criteria have not been met, procedure 500 can branch to step 545, and procedure 500 can continue as shown in FIG. 5.

In 545, another query can be performed to determine if new minimum transmission value $I_n(min)$ is less than the reference minimum transmission value $I_0(min)$ previously established. When the new minimum transmission value $I_n(min)$ is not less than the reference minimum transmission value $I_0(min)$ previously established, procedure 500 can branch to step 550 and can continue as shown in FIG. 5. When the new minimum transmission value $I_n(min)$ is less than the reference minimum transmission value $I_0(min)$ previously established, procedure 500 can branch to step 555, and procedure 500 can continue as shown in FIG. 5.

In 550, another new polarization angle can be established by changing the polarization angle associated with the IMS 100 by a known quantity (<five degrees, and less than previous changed angle) in a second direction that is opposite from the first direction. In addition, another new minimum transmission value $I_N(min)$ can be determined using the steps (530, 535, 540, and 545) as shown in FIG. 5.

In 555, an additional new polarization angle can be established by changing the polarization angle associated with the IMS 100 by a known quantity (<five degrees) in the first direction. For example, the minimum transmission value $I_0(min)$ can be reset to $I_n(min)$. In addition, an additional new minimum transmission value $I_n(min)$ can be determined using the steps (530, 535, 540, and 545) as shown in FIG. 5.

In 560, procedure 500 can end. A graph or a function that relates the minimum transmission value $I_n(min)$ to the polarization angle associated with the IMS 100 and the polarization angle associated with the analyzer subsystem 170 can be determined. The graph or function will have a minimum point, and the minimum point can be used to identify the polarization angle that corresponds to the polarization angle that is in phase or ninety degrees out of phase with the incident plane.

FIG. 6 illustrates an exemplary flow diagram procedure used to determine an optical incident plane of a metrology module relative to the orientation of a structure on a wafer in accordance with embodiments of the invention. For example, the pre-alignment procedure for a metrology module can be performed using IMS 100. In addition, a sample grating direction can be determined relative to the incident plane.

In 610, a measurement anisotropic sample 101 (e.g. a wafer with a grating structure) can be positioned on the alignment subsystem 102 in the IMS 100. For example, the grating structure can designed or selected to have a maximum reflectance contrast between TE mode reflection and TM mode reflection at the incident angle. When a wafer is positioned on the alignment subsystem 102, an alignment element 102a and a wafer notch 101a can be used to align the wafer on the alignment subsystem 102. In addition, the alignment subsystem 102 can be used to locate the diffracted beam (156, 166) and determine the diffraction angle (157, 167).

In 615, the polarization angle associated with the IMS 100 can be set to the minimum polarization angle (minPA(IMS)) determined using procedure 500, and the polarization angle associated with the analyzer subsystem 170 can be set to the minimum analyzer polarization angle (minPA(analyzer)) determined using procedure 500. For example, the polarization angle associated with the IMS 100 and the polarization angle associated with the analyzer subsystem 170 can be set to zero degrees or ninety degrees.

In 620, the wafer orientation angle ($OA_N$) can be measured and stored. For example, the position of the alignment subsystem 102 and the position of the wafer notch 101a can be determined and stored.

In 625, the transmitted light intensity $I(OA_N)$ can be measured using the analyzer subsystem 170 for this wafer orientation angle ($OA_N$).

In 630, the wafer orientation angle ($OA_N$) can be changed using the alignment subsystem 102.

In 635, a query can be performed to determine if a measurement limit has been met. The measurement limit can be the minimum intensity transmitted at some wavelengths, or a mismatch between the measured signal and the simulated signal over a wavelength range. When the measurement limit has been met, procedure 600 can branch to 640, and procedure 600 can continue as shown in FIG. 6. When the measurement limit has not been met, procedure 600 can branch back to 620, and procedure 600 can continue as shown in FIG. 6.

In 640, the measurement data can be examined to determine the wafer orientation that provides the minimum light intensity and/or the wafer orientation that provides the maximum light intensity.

Procedure 600 can end in 645.

FIG. 7 illustrates an exemplary flow diagram procedure used to determine optical incident plane relative to wafer positioning devices in accordance with embodiments of the invention.

In 710, the wafer orientation angle ($OA_{min}$) for the minimum light Intensity or the wafer orientation angle ($OA_{max}$) for the maximum light intensity can be determined.

In 715, the grating orientation can be determined relative to a system reference point. For example, the grating orientation can be determined relative to the position and orientation of the alignment subsystem 102, and the alignment element 102a.

In 720, the incident plane orientation angle for the IMS 100 can be determined using the grating orientation data.

In 725, the relative orientation of the incident plane can be determined relative to the reference point in the IMS 100.

In 730, procedure 700 can end.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention.

Thus, the description is not intended to limit the invention and the configuration, operation, and behavior of the present invention has been described with the understanding that modifications and variations of the embodiments are possible, given the level of detail present herein. Accordingly, the preceding detailed description is not mean or intended to, in any way, limit the invention—rather the scope of the invention is defined by the appended claims.

What is claimed:

1. A method for determining an azimuth angle in an Integrated Metrology Sensor (IMS), the method comprising:
    determining a first function relating minimum transmission values for a high-angle incident beam to polarization angles for a high-angle focusing subsystem in the IMS, wherein the first function has a minimum at a first polarization angle, the first polarization angle being used to determine an incident plane;

determining a second function relating a grating direction to the incident plane associated with the high-angle incident beam;
determining a grating orientation relative to a system reference;
determining an incident plane orientation of the high-angle focusing subsystem using the grating orientation; and
determining the azimuth angle by calculating a relative orientation of the incident plane to the system reference.

2. The method of claim 1, wherein determining the first function further comprises:
   a) establishing a first incident beam using the high-angle focusing subsystem, wherein a first high-angle focusing subsystem is configured to control an input polarization angle associated with the first incident beam;
   b) coupling an analyzer subsystem in the IMS to an output of the high-angle focusing subsystem, wherein the analyzer subsystem is configured to measure the output of the high-angle focusing subsystem and is configured to change polarization angle associated with the analyzer subsystem; and
   c) obtaining the minimum transmission values by changing the input polarization angle associated with the first incident beam and the polarization angle associated with the analyzer subsystem.

3. The method of claim 1, wherein determining the first function further comprises:
   a) establishing a first high-angle incident beam, wherein a first high-angle focusing subsystem in the IMS is configured to control an input polarization angle associated with the first high-angle incident beam;
   b) positioning an isotropic sample on an alignment subsystem in the IMS;
   c) establishing a first high-angle diffracted beam using the isotropic sample;
   d) directing the first high-angle diffracted beam to an analyzer subsystem in the IMS, wherein the analyzer subsystem is configured to measure the directed first high-angle diffracted beam output and is configured to change polarization angle associated with the analyzer subsystem; and
   e) obtaining the minimum transmission values by changing the input polarization angle associated with the first high-angle incident beam and the polarization angle associated with the analyzer subsystem.

4. The method of claim 1, wherein determining the first function further comprises:
   a) positioning an isotropic sample on an alignment subsystem in the IMS;
   b) directing a first high-angle incident beam from the high-angle focusing subsystem to the isotropic sample, the first high-angle incident beam having a first input polarization angle associated therewith;
   c) measuring a diffracted beam from the isotropic sample using an analyzer subsystem in the IMS, wherein the measurement establishes a transmission value, the analyzer subsystem having a variable polarization angle associated therewith;
   d) adjusting the variable polarization angle associated with the analyzer subsystem to obtain a minimum transmission value $I_0(min)$;
   e) establishing a new polarization angle for the first high-angle incident beam;
   f) adjusting the variable polarization angle associated with the analyzer subsystem to obtain a new minimum transmission value $I_n(min)$;
   g) determining the first function relating the minimum transmission values to the polarization angles for the high-angle incident beam, when the new minimum transmission value $I_n(min)$ is less than a first I(min) threshold; and
   h) determining additional minimum transmission values, when the new minimum transmission value $I_n(min)$ is not less than the first I(min) threshold.

5. The method of claim 1, wherein determining the first function further comprises:
   a) establishing a first high-angle incident beam in the IMS, the first high-angle incident beam having a first variable polarization angle associated therewith;
   b) measuring a first diffracted beam using an analyzer subsystem in the IMS, wherein a first transmission value is established;
   c) establishing a first minimum transmission value by changing an analyzer polarization angle associated with the analyzer subsystem;
   d) establishing a new polarization angle for the first high-angle incident beam using a pre-determined difference;
   e) measuring a new diffracted beam using the analyzer subsystem, wherein a new transmission value is established;
   f) establishing a new minimum transmission value by establishing a new analyzer polarization angle associated with the analyzer subsystem;
   g) repeating steps d)-f) to establish a first number of measurement angles, a first number of polarization angles for the first high-angle incident beam, and a first number of new minimum transmission values associated with the first number of measurement angles and the first number of polarization angles for the first high-angle incident beam;
   h) creating the first function using one or more of the minimum transmission values and one or more of the polarization angles for the first high-angle incident beam;
   i) determining one or more minimum values for the first function; and
   j) identifying a zero degree polarization angle and/or a ninety-degree polarization angle using the one or more minimum values for the first function.

6. The method of claim 1, wherein the high-angle incident beam is established using a first set of wavelengths, wherein the first set of wavelengths are between approximately 190 nm and approximately 900 nm.

7. The method of claim 1, wherein determining the second function further comprises:
   a) positioning a grating sample on an alignment subsystem in the IMS;
   b) directing a first high-angle incident beam from the high-angle focusing subsystem in the IMS to the grating sample, the first high-angle incident beam having a first variable polarization angle associated therewith, the first variable polarization angle being determined using the first function;
   c) measuring a diffracted beam from the grating sample using an analyzer subsystem in the IMS, wherein the measurement establishes a wafer orientation angle $(OA_O)$, the analyzer subsystem having a variable polarization angle associated therewith;
   d) rotating the grating sample to establish a new wafer orientation angle $(OA_N)$;
   e) re-measuring the diffracted beam;
   f) repeating steps d)-e) a number of times to establish the second function; and g) determining a minimum wafer orientation angle ($OA_{min}$) associated with a minimum transmission value.

8. The method of claim 1, wherein determining the second function further comprises:
   a) positioning a grating sample on an alignment subsystem in the IMS;
   b) directing a first high-angle incident beam from the high-angle focusing subsystem in the IMS to the grating sample, the first high-angle incident beam having a first variable polarization angle associated therewith, the first variable polarization angle being determined using the first function;
   c) measuring a diffracted beam from the grating sample using an analyzer subsystem in the IMS, wherein the measurement establishes a wafer orientation angle ($OA_0$), the analyzer subsystem having a variable polarization angle associated therewith;
   d) rotating the grating sample to establish a new wafer orientation angle ($OA_N$);
   e) re-measuring the diffracted beam;
   f) repeating steps d)-e) a number of times to establish the second function; and
   g) determining a maximum wafer orientation angle ($OA_{max}$) associated with a maximum transmission value.

9. The method of claim 1, wherein creating the high-angle incident beam further comprises:
   a) coupling the high-angle focusing subsystem to a first reflection subsystem;
   b) coupling the first reflection subsystem to a first selectable reflection subsystem; and
   c) coupling the first selectable reflection subsystem to a beam generator subsystem having one or more output beams associated therewith, the first selectable reflection subsystem directing one or more of the output beams to the first selectable reflection subsystem when the IMS is operating in a first mode.

10. The method of claim 9, wherein a lamp subsystem and a reference subsystem are coupled to the beam generator subsystem.

11. A method for determining an azimuth angle in an Integrated Metrology Sensor (IMS), the method comprising:
   determining a first function relating minimum transmission values to polarization angles for a low-angle incident beam created by a low-angle focusing subsystem in the IMS, wherein the first function has a minimum at a first polarization angle, the first polarization angle being used to determine an incident plane;
   determining a second function relating a grating direction to the incident plane associated with the low-angle incident beam;
   determining a grating orientation relative to a system reference;
   determining an incident plane orientation of the low-angle focusing subsystem using the grating orientation; and
   determining the azimuth angle by calculating a relative orientation of the incident plane to the system reference.

12. The method of claim 11, wherein determining the first function further comprises:
   a) establishing a first incident beam using the low-angle focusing subsystem, wherein a first low-angle focusing subsystem is configured to control an input polarization angle associated with the first incident beam;
   b) coupling an analyzer subsystem in the IMS to an output of the low-angle focusing subsystem, wherein the analyzer subsystem is configured to measure the output of the low-angle focusing subsystem and is configured to change polarization angle associated with the analyzer subsystem; and
   c) obtaining the minimum transmission values by changing the input polarization angle associated with the first incident beam and the polarization angle associated with the analyzer subsystem.

13. The method of claim 11, wherein determining the first function further comprises:
   a) establishing a first low-angle incident beam, wherein a first low-angle focusing subsystem in the IMS is configured to control an input polarization angle associated with the first low-angle incident beam;
   b) positioning an isotropic sample on an alignment subsystem in the IMS;
   c) establishing a first low-angle diffracted beam using the isotropic sample;
   d) directing the first low-angle diffracted beam to an analyzer subsystem in the IMS, wherein the analyzer subsystem is configured to measure the directed first low-angle diffracted beam output and is configured to change polarization angle associated with the analyzer subsystem; and
   e) obtaining the minimum transmission values by changing the input polarization angle associated with the first low-angle incident beam and the polarization angle associated with the analyzer subsystem.

14. The method of claim 11, wherein determining the first function further comprises:
   a) positioning an isotropic sample on an alignment subsystem in the IMS;
   b) directing a first low-angle incident beam from the low-angle focusing subsystem to the isotropic sample, the first low-angle incident beam having a first input polarization angle associated therewith;
   c) measuring a diffracted beam from the isotropic sample using an analyzer subsystem in the IMS, wherein the measurement establishes a transmission value, the analyzer subsystem having a variable polarization angle associated therewith;
   d) adjusting the variable polarization angle associated with the analyzer subsystem to obtain a minimum transmission value $I_0(min)$;
   e) establishing a new polarization angle for the first low-angle incident beam;
   f) adjusting the variable polarization angle associated with the analyzer subsystem to obtain a new minimum transmission value $I_N(min)$;
   g) determining the first function relating the minimum transmission values to the polarization angles for the low-angle incident beam, when the new minimum transmission value $I_N(min)$ is less than a first I(min) threshold; and
   h) performing additional measurements, when the new minimum transmission value $I_N(min)$ is not less than the first I(min) threshold.

15. The method of claim 11, wherein determining the first function further comprises:
   a) establishing a first low-angle incident beam in the IMS, the first low-angle incident beam having a first variable polarization angle associated therewith;
   b) measuring a first diffracted beam using an analyzer subsystem in the IMS, wherein a first transmission value is established;
   c) establishing a first minimum transmission value by changing an analyzer polarization angle associated with the analyzer subsystem;

d) establishing a new polarization angle for the first low-angle incident beam using a pre-determined difference;
e) measuring a new diffracted beam using the analyzer subsystem, wherein a new transmission value is established;
f) establishing a new minimum transmission value by establishing a new analyzer polarization angle associated with the analyzer subsystem;
g) repeating steps d)-f) to establish a first number of measurement angles, a first number of polarization angles for the first low-angle incident beam, and a first number of new minimum transmission values associated with the first number of measurement angles and the first number of polarization angles for the first low-angle incident beam;
h) creating the first function using one or more of the minimum transmission values and one or more of the polarization angles for the first low-angle incident beam;
i) determining one or more minimum values for the first function; and
j) identifying a zero degree polarization angle and/or a ninety-degree polarization angle using the one or more minimum values for the first function.

16. The method of claim 11, wherein the low-angle incident beam are established using a first set of wavelengths, wherein the first set of wavelengths are between approximately 190 nm and approximately 900 nm.

17. The method of claim 11, wherein determining the second function further comprises:
a) positioning a grating sample on an alignment subsystem in the IMS;
b) directing a first low-angle incident beam from the low-angle focusing subsystem in the IMS to the grating sample, the first low-angle incident beam having a first variable polarization angle associated therewith, the first variable polarization angle being determined using the first function;
c) measuring a diffracted beam from the grating sample using an analyzer subsystem in the IMS, wherein the measurement establishes a wafer orientation angle ($OA_0$), the analyzer subsystem having a variable polarization angle associated therewith;
d) rotating the grating sample to establish a new wafer orientation angle ($OA_N$);
e) re-measuring the diffracted beam;
f) repeating steps d)-e) a number of times to establish the second function; and
g) determining a minimum wafer orientation angle ($OA_{min}$) associated with a minimum transmission value.

18. The method of claim 11, wherein determining the second function further comprises:
a) positioning a grating sample on an alignment subsystem in the IMS;
b) directing a first low-angle incident beam from the low-angle focusing subsystem in the IMS to the grating sample, the first low-angle incident beam having a first variable polarization angle associated therewith, the first variable polarization angle being determined using the first function;
c) measuring a diffracted beam from the grating sample using an analyzer subsystem in the IMS, wherein the measurement establishes a wafer orientation angle ($OA_0$), the analyzer subsystem having a variable polarization angle associated therewith;
d) rotating the grating sample to establish a new wafer orientation angle ($OA_N$);
e) re-measuring the diffracted beam;
f) repeating steps d)-e) a number of times to establish the second function; and
g) determining a maximum wafer orientation angle ($OA_{max}$) associated with a maximum transmission value.

19. The method of claim 11, wherein creating the low-angle incident beam further comprises:
a) coupling the low-angle focusing subsystem to a first reflection subsystem;
b) coupling the first reflection subsystem to a first selectable reflection subsystem; and
c) coupling the first selectable reflection subsystem to a beam generator subsystem having one or more output beams associated therewith, the first selectable reflection subsystem directing one or more of the output beams to the first selectable reflection subsystem when the IMS is operating in a first mode.

20. The method of claim 19, wherein a lamp subsystem and a reference subsystem are coupled to the beam generator subsystem.

* * * * *